United States Patent [19]

Patel

[11] Patent Number: 5,558,701

[45] Date of Patent: Sep. 24, 1996

[54] SOL-GEL COMPOSITION FOR PRODUCING GLASSY COATINGS

[75] Inventor: Bipin C. M. Patel, Greenford, England

[73] Assignee: British Technology Group Limited, London, England

[21] Appl. No.: 448,483

[22] PCT Filed: Jan. 5, 1994

[86] PCT No.: PCT/GB94/00015

§ 371 Date: Jul. 25, 1995

§ 102(e) Date: Jul. 25, 1995

[87] PCT Pub. No.: WO94/15882

PCT Pub. Date: Jul. 21, 1994

[30] Foreign Application Priority Data

Jan. 8, 1993 [GB] United Kingdom .................. 9300261

[51] Int. Cl.⁶ .................. C09K 3/00; A61K 6/093
[52] U.S. Cl. .................. 106/35; 433/217.1; 433/226; 501/12; 252/315.6; 252/315.7
[58] Field of Search .................. 106/35; 433/217.1, 433/226; 501/12; 252/315.6, 315.7

[56] References Cited

U.S. PATENT DOCUMENTS

| | | |
|---|---|---|
| 3,847,583 | 11/1974 | Dislich et al. . |
| 4,431,451 | 2/1984 | Mabie et al. . |
| 5,068,208 | 11/1991 | Haun et al. . |
| 5,433,941 | 7/1995 | Patel ........................................ 106/35 |
| 5,433,956 | 7/1995 | Patel ........................................ 106/35 |

FOREIGN PATENT DOCUMENTS

4482659A1  4/1992  European Pat. Off. .

*Primary Examiner*—Karl Group
*Attorney, Agent, or Firm*—Nixon & Vanderhye

[57] ABSTRACT

Glassy coatings are made by curing in situ a coating of a sol gel of boron triethoxide, water, alcohol, and the alkoxides of: titanium and zirconium. A platey filler such as mica is present. The coating may be applied to teeth as a dental fissure sealant or varnish to protect restorations, or as an inherently coloured cosmetic coating, or as a prophylactic coating.

32 Claims, No Drawings

SOL-GEL COMPOSITION FOR PRODUCING GLASSY COATINGS

This invention relates to a sol gel composition for use in producing glassy coatings, to a process for producing a glassy coating using the composition, to a method For cosmetic colouring of teeth using the process and to a method for prophylactic protection of teeth using the process.

Fissure sealants have been demonstrated as effective in reducing incidence of tooth decay and inhibiting decay even after it has started, but have not gained universal acceptance in general practice. These fissure sealants are understood to have relatively low durability, adhering to the tooth with a rather short half-life (5 years).

Sol-gels would not be considered for dental use, since the curing of sol gels is typically undertaken in a slow furnace, which would pose clinical difficulties. Thus, U.S. Pat. No. 5,068,208 discloses a method of making optical elements of gradient-index glass by a sol-gel route including adding together a partially hydrolysed silicon alkoxide, an alkoxide of Ti or Zr, and an alkoxide of B, Al or Ge, adding water while agitating, moulding the mixture for sufficient time to form a gel, washing the moulded gel, acid-leaching the washed gel to remove some metal oxide, fixing the gel in aqueous alcohol, drying the gel and sintering.

Silicon-based sol gels often rely on the presence of sodium alkoxide, and it has been suggested that sodium does not enhance the chemical resistance or mechanical durability of glass. However, an alternative is taught by EP-A-482659, in which a thin glass film is produced on a substrate by a sol-gel method, comprising applying to the substrate a hydrolysable solution containing a metal alkoxide, water, alcohol and an acid, exposing to ammonia and heating to form a thin glas film in situ. The metal alkoxide is selected from Si, Ti, Ge, Al and B, of which Si, and Si+Ti, are exemplified.

According to the present invention, a sol gel, xerogel or heat-consolidated gel composition comprises: a hydrolysable boron ester (such as boron triethoxide or tripropoxide) or boron salt convertible to the oxide by thermal or oxidative decomposition (such as boron nitrate or citrate); a solvent (alcoholic or non-alcoholic); alkoxide(s) of any one, two or more of aluminium and of Gp VB and/or GpIVB metals (preferably zirconium together with titanium); and a filler having a mean particle size of up to 3 µm in one dimension and 5–100 µm in the other two dimensions. Part of the boron ester can be substituted by appropriate compounds of other non-metallic glass formers. Some of these compositions have been found to be usefully stable. Where not deleterious, a GpIA or IIA metal alkoxide (such as sodium or calcium) may be present. Some or all of such metal may advantageously be present as the fluoride. Preferably the number of metals present (not counting B or Si) is at least two, e.g. three or four, of which one is preferably Ti. The composition may further comprise water, which may however be supplied otherwise, e.g. by exposure to air. The metal alkoxide, if there is just one, may be Ti or Zr or Al. Preferred combinations of metal alkoxides are: (i) Zr, Ti; (ii) Al, Ti, Na; (iii) Ti, Na, Zr; (iv) Al, Ti, Zr; and (v) Al, Ti, Zr, Na. The metals (not counting Na) are preferably present in amounts up to one-sixth (by number of atoms) of the boron. Solid oxides e.g. fine neodymium oxide powder may be dispersed into the sol gel.

Preferably, the sol gel composition synthesis was characterised by an ageing step, during which moisture was admitted to the composition at a rate under 1% of the rate in free air. This controls the rate of hydrolysis and consequently of 'polymerisation' of the molecules of the composition without destabilisation, which rate can in principle be monitored via an increase in viscosity of the composition, or e.g. by infra-red spectroscopy, by differential scanning calorimetry, by thermogravimetric analysis, by nuclear magnetic resonance or by electron spin resonance.

The filler may be for example laponite, zeolite, kaolinite or vermiculite, or preferably the filler is in the form of flat plates such as talc or mica, or a mixture, optionally coated (preferably by chemical vapour deposition) with for example titanium dioxide, chromium oxide or ferric oxide or a mixture. Such materials are harmless if swallowed in the small quantities in which they might spall off. The filler preferably comprises up to 30% by weight of the composition, and more particularly preferably comprises 20–30 wt % where the sol gel proportion of the composition is a sol gel yielding 5 to 15 (e.g. 10) wt % on curing, and the filler preferably comprises 5–10 wt % where the composition yields 0.1–1 wt % on curing.

Other coating methods may also be used, alternatively or in addition, such as deposition of silane. This can promote adhesion and enhance mechanical properties. As silanising agents, compounds containing a glycidoxy organic group and a trimethoxysilyl group may be used, such as Dow Corning Z6040 (trade mark),

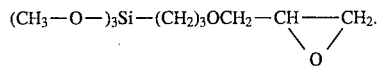

The mean filler particle size is preferably 0.1 to 2 µm in one dimension and 5–100 µm in the other two dimensions. Where the latter dimensions are 5–20 µm, and the sol gel preferably yields 5–15 e.g. 10 wt % on curing, the filler preferably comprises from 20 to 30% by weight of the composition (i.e. before curing), and will be suitable for single-coating applications, to mask tooth discolourations. Where those dimensions are 10–60 µm, the filler preferably comprises 10–20% by weight of the composition. In the case of xerogel, which is 90 volume % air, a platey filler will improve its mechanical properties such that it could be used as an insulating material, or the cavities can be used as drug reservoirs, which will slowly release, on a tooth or otherwise. Where the sol gel yields 0.1–1 wt % on curing and the filler is correspondingly preferably 5–10 wt %, a better performance is often obtained, and the sol gel may be applied in multiple coatings to the tooth.

The filler reduces the incidence of crazing in the cured sol-gel (not only in dental applications) by physically reducing the bulk of sol gel needed, thus making what there is of it more elastic. It also absorbs incident laser energy and re-emits it to the sol gel, accelerating the latter's curing. The filler also improves the abrasion resistance of the cured sol gel glassy coating. Given that the yield of glass from sol-gels is preferably about 5–10% by weight, and can be 0.1 to 1% or even less as already indicated, the filler when present will in such cases thus be a major component of the product. In the case of mica, which tends to fall out of sol-gel suspension quite rapidly, it may be incorporated into the sol-gel when or immediately after the latter is made up; as the sol-gel 'polymerises', the polymers grow on the mica, improving its suspension and bonding, but as a precaution it may be advisable to shake it before use, or else the mica may be added to the sol gel at any later stage, e.g. immediately before use. On the other hand, a too-perfect suspension is to be avoided; as it is, the mica advantageously settles into pits and fissures, whither it is drawn by surface tension.

The hydrolysable boron ester is preferably boron triethoxide or boron tripropoxide, or any other boron alkoxide may be used. The molar proportion of water:boron may be (¾ to 3):1, preferably (1 to 2):1, for example 1½:1. To induce successful hydrolysis in the composition, water must be added homogeneously to prevent localised excesses leading to precipitation. For example, water may be added by stirring the composition vigorously under an atmosphere of high humidity, or by allowing the composition to stand in a sealed container with a few pinholes to allow very slow ingress of atmospheric moisture. Part of the B, as already mentioned, can be substituted by appropriate compounds of other non-metallic glass formers. Boron nitrates or boron citrate, optionally esterified, may be tried. The solvent may comprise hydrophobic materials such as partly or wholly halogenated methane, e.g. $CCl_4$, or tetrahydrofuran, or diethylether, or hydrophilic materials such as ketones e.g. acetone or alcohols e.g. ethanol optionally containing up to an equal volume of propanol (iso or n) preferably from ½ to ¾ volumes (e.g. 60 ethanol:40 propanol). The proportion of water plus solvent may be such that the composition yields 1–10 g boron oxide per 100 g (the filler being included in the 100 g). In an alternative sol-gel preparation method, solvents (including water) may be absent and an intermediate solid may be converted into an applyable liquid sol gel composition by controlled exposure to atmospheric moisture.

A process for producing a glassy coating according to the invention comprises applying a sol gel composition e.g. as set forth above, to an object to be coated and curing the coating e.g. by flame (very miniature flames can be used in the mouth) e.g. butane flame heating, otherwise by radiation from the tip of a diathermy needle or preferably by laser, for example a $CO_2$ laser, with an energy input to the object of preferably 1 to 2000 $mJ/mm^2$ preferably applied at a rate which does not cause overheating leading to cracking or flaking of the film, e.g. a travelling spot of e.g. 150 µm diameter illuminating any one point for from e.g. ½ to 100 milliseconds such as 20 to 60 ms, the laser having a power of such as under 4W (more preferably up to 1W), preferably for a duration of 0.1 to 4 (e.g. ½ to 3) seconds. This energy input is expected to raise the overall tooth temperature by only 1°–2C°, excess heat being removed by the blood supply to the pulp. A $CO_2$ laser may be tuned to 10.6 µm as is most usual, or may be tuned to or near 9.6 µm (e.g. 9½–10 µm), which is most strongly absorbed by natural tooth, and may be of pulsed output. This is useful if it is desired to fuse (physically incorporate) the sol gel into the enamel or dentine by temporarily or permanently vitrifying these, a procedure which requires high laser power outputs and which is expected to make the enamel more resistant to caries. The pulse width and frequency can be varied to suit the thickness of the film to achieve good consolidation, and, if desired, vitrification. An Nd:YAG 1.06 µm laser could be used, but needs a chromophore in the sol gel to absorb it. More generally, the radiation should be of a wavelength which is totally absorbed and converted to heat within the sol gel and first few underlying microns of the tooth or other substrate. Apart from the quoted examples of $\lambda=10.6$ µm and 1.06 µm, the mid infra-red range of $\mu\approx2$ to 6 µm (e.g. 5 µm) may be used. The coating as applied (before curing) may be up to 30 µm thick, preferably 1–10 µm e.g. 2–10 µm. The preferred energy input of 1 to 2000 $mJ/mm^2$ thus includes a preferred range where only consolidation of the film is required, e.g. 20 to 500 such as 50 to 200 $mJ/mm^2$, and a preferred range where vitrification of part of the substrate tooth is required, e.g. 500 to 2000 $mJ/mm^2$.

A method for cosmetic colouring of a tooth according to the invention comprises using the process set forth above, wherein the said object is the tooth. The tooth may have been treated with restorative material such as glass alkenoate cement, for which the present invention can be regarded as providing a protection. The sol-gel may include a pigment. The neodymium oxide powder suggested above imparts a remarkably evenly distributed blue colour to the glass. Alternatively, preferably the filler is so formulated as to appear a tooth-like colour in the applied thickness. Alternatively, the tooth is stained cosmetically, and the stain retained by the applied coating. As a side-effect, prophylactic benefits may be obtained.

A method for prophylactic protection of a tooth according to the invention comprises using the process set forth above, wherein the said object is the tooth. The tooth may have been treated with restorative material such as glass alkenoate cement, for which the present invention can be regarded as providing a varnish. Preferably the filler is so formulated as to appear a tooth-like colour in the applied thickness. As a side-effect in that case, cosmetic benefits may be obtained. In all these methods, the option (explained above) of fusing tile enamel, at least superficially, may be adopted.

Preferably the tooth is cleaned beforehand e.g. mechanically or by acid-etching.

The present invention provides a method whereby drugs may be released slowly, comprising allowing a coating produced by xerogel as set forth above and charged with the drug to ablate.

The two forms of product derived from sol-gel, viz glass and xerogel, differ in the physical organisation of their polymeric structures:

(i) Sol-Gel derived glass: A high density polycondensed lattice or network with minimal porosity.

(ii) Sol-Gel derived xerogel: A polymeric structure which is highly porous in the 100 nm range and of correspondingly low density, having trapped organic residues and being mechanically weak. The formation of a xerogel is a direct indication of sufficient hydrolysis to yield a useful glassy material. The deposition of a thin film from these sol-gels will depend upon dilution factor and nature of the solvents used. It is important to note these sol-gels once synthesised will continue to undergo hydrolysis and condensation.

Defect free glassy films are important for adequate tooth protection, and require careful attention to two crucial stages in the sol-gel process once a continuous liquid coating has been applied:

(i) Sol liquid-to-gel transition (ii) Consolidation of gel to glass.

Stage (i) needs to be slow which implies controlled rate of solvent loss, otherwise the shrinkage of resulting gel is rapid and uneven leading to a fractured coating. The gel has to be partially dried and then given even surface heat treatment. Stage (ii), viz heat treatment, also needs to be carefully controlled, otherwise the film will crack and/or blister. The glass coating is vulnerable to cracking during heat treatment where shrinkage occurs, as density increases, mainly in the vertical direction and not the horizontal. Thin coatings that are less than ¼ µm generally do not suffer from cracking and have better mechanical durability. Following this finding, efforts to develop a sol gel glass having the same coefficient of thermal expansion as natural tooth were discontinued as unnecessary.

Using liquid spreading techniques likely to be available in ordinary clinical practice would however yield unconsolidated coatings on tooth surfaces having a thickness of approximately 1–20 e.g. 5–10 µm. (Applying a drop from a dropwise dispenser, it spreads across the tooth surface spontaneously.) As indicated above, the addition of inert fillers such as mica flakes is desirable; it permits thicker yet crack-free consolidated glass coatings and improves xerogel coatings. Curing gives rise to a consolidated film which is thinner than the unconsolidated coating because of loss of solvent and organic constituents. Allowing for this, an ideal post-curing (consolidated) film thickness to aim for is e.g. 0.1 to 1 μm. Sol-gel derived coatings may be applied to:

(i) Fissure sealing
(ii) Sealing marginal gaps arising from old restorations
(iii) Entire tooth crown surface protection
(iv) Root canal therapy, e.g. sealing tubules
(v) Lining freshly prepared cavities (blocking open tubules
(vi) Protection of cavities freshly restored with filling materials.
(vii) Replacing the use of porcelain veneers for aesthetically coating discoloured enamel surfaces
(viii) Slow release of fluoride for topical application to tooth
(ix) Controlled release of drugs for example in the treatment of dentine hypersensitivity or periodontal disease, and
(x) Impregnation of porous structures for mechanical strengthening and other purposes e.g. drug release, enamel disorders and dental material improvement.

There are certain preferred ranges of compositions of the sol-gel. Considering atoms of B, Na (or equivalent), Al, Zr and Ti (or equivalent), boron preferably accounts for at least 40, more preferably at least 50%. Sodium is preferably under 50% (on an atomic basis again) such as 1–40%, more preferably 5–30%. Aluminium may be 5–15%, and titanium and/or zirconium and/or vanadium and/or niobium and/or tantalum 3–15%, more preferably 5–10%, and/or not exceeding one-fifth of the boron. Boron is desirable as a glass-former, and sodium should be limited as it makes the glass less resistant to acid.

The invention will now be described by way of example. Boron alkoxides were made as follows.

1 Boron Triethoxide

Boron trialkoxide can be synthesised by the dehydration of mixtures of alcohol with boric oxide (equation 1) or boric acid (equation 2). The reactions are both slow and require long reflux times.

$$B_2O_3+6ROH \rightarrow 2B(OR)_3+3H_2O \qquad 1$$

$$B(OH)_3+3ROH \rightarrow B(OR)_3+3H_2O \qquad 2$$

Boric acid and ethanol (eq2) were used to synthesise boron triethoxide. The mixture was refluxed with continuous stirring. 1:3 mole of boric acid to ethanol was used.

|  | Required | Used |
| --- | --- | --- |
| B(OH)$_3$ (white solid) | 61.83 g (1 mole) | 61.00 g |
| Ethanol | 138 g (3 moles) | 138.38 g |

The above mixture was refluxed for 34 hours and on cooling a white solid (boric acid) remained unreacted; a small percentage appeared to precipitate out of solution. The reflux temperature was found to be 80°–81° C. A sample of 10 ml was taken after 24 hours of refluxing, which on cooling begins to flocculate. A white semi-gelatinous precipitate results, leading then to a suspension. On standing the precipitate settles out leaving a separate clear liquid above the white precipitate. The clear liquid was decanted and stored for future use. The clear liquid, on evaporation, produced a white solid which is thought to be the required alkoxide mixed with boron oxide.

The clear liquid is thought to be composed of a mixture of boron triethoxide, ethanol and water, which on access to moisture from the atmosphere and loss of solvent leads to gelling and boron oxide formation.

1000 μl of the above clear liquid has a mass of 0.802 g, and produces 0.081 g of white solid on evaporation to dryness, that is a yield of 10.1%.

2 Boron Tripropoxide

Conditions: Reflux With Continuous Stirring.

Excess propanol was used in an attempt to increase the yield of boron tripropoxide. (1:6 mole used).

|  | Required | Used |
| --- | --- | --- |
| B(OH)$_3$ Boric acid | 30.91 g (0.5 moles) | 31.8 g |
| Propan-1-ol | 180 g (3 moles) | 180.7 g | total reflux time 6 hours, temperature approximately 82° C.

Synthesis stage 1, 3 hours reflux with only 90 g of propanol then further 90 g of propanol was added and refluxed for a further 3 hours.

The 1000 μl of supernatant has a mass of 0.7 g (3 hrs reflux with 1:3 mole reaction) and yields 0.07 g of solid, that is 10%.

It is again assumed the above supernatant is composed of a mixture of boron alkoxide, alcohol and water.

Synthesis of Boron Based Sol-Gels

Series I

The above synthesised boron alkoxide will be used as the precursor for boron oxide.

The following metal alkoxides have been investigated.
Titanium tetraisoproxide (liq)
Zirconium tetra sec-butoxide (liq) 80% in butanol
Boron triethoxide (liq) in ethanol
Boron tripropoxide (previously made) in propanol

EXAMPLE 1

Ethanol+Ti+Zr+B

The order of addition of the components and their respective amounts were as follows:

| Ethanol + | 2.331 g | (3000 μl) |
| --- | --- | --- |
| Ti tetraisopropoxide + | 0.369 g | (400 μl) |
| Zr tetra sec butoxideq + | 0.278 g |  |
| Boron triethoxide solution described above |  | (600 ml) |

Ethanol+Ti+Zr produced a clear liquid but the addition of the boron triethoxide produced a white precipitate which remains in suspension. The product was however of some utility.

EXAMPLE 2

Ethanol+Ti+B+Zr

The order of addition of the components and their repective amounts were as follows:

| Ethanol + | 2000 μl |
|---|---|
| Ti tetraisopropoxide + | 0.373 g (400 μl) |
| Boron triethoxide solution + | 0.144 g (200 μl): A white precipitate appeared |
| Zr tetra sec butoxide | 4.255 g: On shaking, the precipitate redissolves, a phenomenon requiring a certain minimum Zr above that in Example 1. |

A xerogel was then made from this solution.

1000 μl of the solution was exposed slowly to atmospheric moisture in a 25 ml glass bottle closed with a perforated (pin holes) cap.

Observations:

24 hours Approximately 50% of the liquid had evaporated and the sol-gel system remained clear.

4 days The sol-gel system set to a fractured white gel-like material approximately 10–20% of the original volume. Clear flakes had formed on the inner side walls of the glass bottle. This is a clear indication of the formation of a xerogel from solution adhering to the side walls and having evaporated.

This sol-gel can thus yield clear xerogel material and/or a white 'xerogel-like material'.

EXAMPLE 3

Ethanol+Ti+Zr

The order of addition of the components and their respective amounts were as follows:

a higher quantity of Ti & B and a smaller quantity of Zr.

| Ethanol + | 4000 μl |
|---|---|
| Ti tetraisopropoxide + | 0.940 g (1000 μl) |
| Boron triethoxide in ethanol + | 0.801 g (1000 μl) of the solution described at the outset of the Examples |
| Zr tetra sec butoxide | 2.139 g |

The ethanol+Ti+B produces an intense white precipitate suspension. Addition of Zr and vigorous shaking for 1 minute leads to total dissolution of the white precipitate yielding a clear solution with a yellow hue (due to the inherent yellow colour of Zr tetra sec butoxide solution).

The white precipitate was not identified, but titanium dioxide is ruled out (because it is insoluble) and titanium ethoxide is ruled out because it is miscible with ethanol.

A xerogel was then made from this solution.

1000 μl of the solution was exposed slowly to atmospheric moisture in a 25 ml glass bottle closed with a perforated (pin holes) cap.

Observations:

24 hours later Approximately 50% of the liquid had evaporated and the sol-gel had set to a white gel-like material.

4 days later The white gel-like material dried out and fractured. There was also a presence of clear flakes of a xerogel peeling from inner walls of the glass container.

This sol-gel can thus yield clear xerogel and/or a white 'xerogel-like material'.

EXAMPLE 4

From the yellow-hued clear solution of Example 3, 1000 μl was taken. To it were added successive aliquots of 100 μl of boron ethoxide solution in ethanol (0.08 g boron ethoxide per aliquot). The first four aliquots were added without any sign of turbidity (precipitate/suspension formation) and the system remained clear. With the fifth and sixth aliquots, the system became slightly turbid and opaque with possibly a slight increase in viscosity. From the seventh to the tenth aliquot the system progressively became turbid and viscous and a white precipitate/suspension formed which set to gel within 3–5 minutes of adding the final aliquot of boron triethoxide. The system tolerated more boron with these successive small additions than when the same amount of boron was added all at once.

EXAMPLE 5

Ethanol+B+Zr+Ti

The order of addition of the components and their respective amounts were as follows:

| Ethanol + | 2000 μl |
|---|---|
| Boric triethoxide + | 1.641 g |
| Zr tetra sec butoxide + | 1.698 g |
| Ti tetraisopropoxide | 4.600 g |

Ethanol+Boric triethoxide+Zr produces an intense white precipitate/suspension. The addition of excess Ti and vigorous shaking leads to complete dissolution of the precipitate and the reaction is noticeably exothermic.

From this and Example 4, it appears that both Ti and Zr induce the gel/precipitate formation (most likely to be B(—O—)n complex) which in the presence of a certain level of Ti or Zr alkoxide leads to complete dissolution and a clear stable sol-gel.

A simple Boron+Zirconium sol-gel via this route does not seem to be possible.

A xerogel was then made from this solution.

1000 μl of the solution was exposed slowly to atmospheric moisture in a 25 ml glass bottle closed with a perforated (pin holes) cap.

Observations:

24 hrs 50% volume loss, sol-gel remained clear 4 days Set as previously to a fractured white gel-like material which dehydrates to a white fractured solid. There was also the presence of clear flakes of xerogel material peeling off the container walls.

1000 μl yielded 0.301 g of white xerogel-like solid.

The 0.301 g solid was heated to 1080° C. for 2.5 hours and yielded 0.137 g of a fractured white ceramic-like material.

This sol-gel can thus yield clear xerogel and/or a white xerogel-like material.

EXAMPLE 6

Ethanol+B+Ti+Zr

The order of addition of the components and their respective amounts were as follows:

| | |
|---|---|
| Ethanol + | 2000 μl |
| Boron triethoxide + | 1.634 g (2000 μl) |
| Titanium tetraisopropoxide (pure) + | (2000 μl) |
| Zr tetra sec butoxide | first addition 2.134 g and second addition making it up to 4.773 g. |

The first addition of Zr did not clear the suspension but the second addition of Zr taking the total amount to 4.773 g completely cleared the suspension resulting in a clear yellow-hued sol-gel.

A xerogel was then made from this solution.

1000 μl of the solution was exposed slowly to atmospheric moisture in a 25 ml glass bottle closed with a perforated (pin holes) cap.

Observations 24 hrs Approximately 50% reduction in volume: the sol-gel remained clear.

4 days A fractured white solid resulted. Flakes of clear xerogel were also present.

This sol-gel can thus yield clear xerogel and/or a white 'xerogel-like material'.

EXAMPLE 7

Si+Al+Ti+Na+Zr+B

A previously synthesised stable sol-gel was used which had been given limited access to atmospheric moisture for 19 days during synthesis. This had the composition:

Tetraethoxysilicon 99.62 g

Zr tetra sec butoxide 11.2 g (i.e. 13.79 g of an 80% solution in butan-1-ol)

Al tetra sec butoxide 19.87 g

Na ethoxide 9.3g

This yielded a semi-solid, then eventually a clear liquid.

To 1000 μl of this Si+Al+Ti +Na +Zr sol-gel was added 200 μl of boron triethoxide solution. No reaction was observed and the system remained clear. 1000 μl of the liquid was exposed slowly to atmospheric moisture in a 25 ml glass bottle closed with a perforated (pin holes) cap.

Observations:

2 hrs The sol-gel remained clear 24 hrs The sol-gel remained clear but has become viscous.

48 hrs The sol-gel remained clear and viscous.

72 hrs Set to a clear semi-gel/solid state 96 hrs Set to a clear solid (xerogel state)

144 hrs Clear solid, i.e. xerogel

EXAMPLE 8

Si+Ti+Al+Na+B (NB no zirconium)

A previously synthesised stable sol-gel was used which, after 4 days' exposure, was sealed in a vessel and stored at −10° C. for over a year. This sol-gel had the composition:

Tetra ethoxysilicon (TEOS) 66,15 g

Ti tetra isopropoxide 26.68 g

Al tetra sec butoxide 24.42 g

Na ethoxide 9.06 g and had been made in this order of mixing: TEOS+Al +Ti (still a clear liquid) then+Na produces a precipitate/gel-like mass. Limited exposure to atmospheric moisture led to conversion from solid state to a stable usable liquid.

To 1000 μl of this stable usable liquid was added 600 μl of boron triethoxide.

The system remained clear and appeared to be stable.

1000 μl of the liquid was exposed slowly to atmospheric moisture in a 25 ml glass bottle closed with a perforated (pin holes) cap.

Observations:

12 hours The sol-gel remained clear 24 hours The sol-gel remained clear but had become viscous.

48 hours The sol-gel remained clear and viscous.

72 hours Set to a clear semi-gel/solid consistency 96 hours Set to a clear solid (xerogel state)

144 hours Continued to lose solvent, became fractured.

EXAMPLE 9

B+Zr+Ti+Na

To 2000 μl of the clear solution of Example 6 (light yellow in colour) was added 0.167 g sodium ethoxide (yellow powder).

The sodium ethoxide only dissolved sparingly producing a more strongly yellow/orange-coloured solution. A large proportion of the sodium ethoxide did not dissolve. Propanol (200 μl) was added to dilute the solution and aid dissolution of the sodium ethoxide. There were no adverse reactions to propanol, almost all of the sodium ethoxide dissolving to yield a strongly yellow/orange liquid.

Excess sodium ethoxide appeared to continue to dissolve over the next 1–3 hours. There then appeared to be signs of turbidity in the sol-gel, but the turbidity clears in time.

A xerogel was then made from this solution.

1000 μl of the solution was exposed slowly to atmospheric moisture in a 25 ml glass bottle closed with a perforated (pin holes) cap.

Observations:

24 hours Remained as a clear liquid 96 hours Set to a solid gel-like clear material, with also a clear xerogel coating on the side walls of the glass bottle.

EXAMPLE 10

B+Zr+Ti+Al

To 1000 μl of the clear solution of Example 6 (yellow coloured liquid) was added 0.269 g of aluminium tripropoxide (clear viscous liquid).

This produced an exothermic reaction on mixing. A semi-gelatinous liquid resulted which was semi-translucent. Propanol (3000 μl) was added to dilute the system; no adverse reactions were observed. Within 5–10 minutes of shaking/mixing, a clear transparent yellow liquid resulted.

A xerogel was then made from this liquid.

1000 μl of the liquid was exposed slowly to atmospheric moisture in a 25 ml glass bottle closed with a perforated (pin holes) cap.

Observations 12 hours Remained as clear liquid 24 hours Set to a white gel-like solid. There was also a presence of clear flakes of xerogel.
96 hours White fracture xerogel-like solid resulted, together with a clear xerogel coating on the side walls of the glass bottle.

EXAMPLE 11

B+Ti+Al

| | |
|---|---|
| Boron isopropoxide 4.004 g + | (5000 μl) |
| Titanium isopropoxide 2.864 g + | (3000 μl) |
| Aluminium sec-butoxide 3.121 g | |

The mixture remained a clear liquid at all stages, suggesting the utility of boron isopropoxide as a sol gel component of compositions according to the invention, and also suggesting the possibility of a B/Ti sol gel.

The yield in B was about 13%, and is typically 10-13%.

I claim:

1. A sol gel, xerogel or heat-consolidated gel composition comprising a hydrolyzable boron ester; a solvent; a metal alkoxide(s) of one or more metals selected from the group consisting of: Al, GpVB metals, and GpIVB metals; and a filler having a mean filler particle size of up to 3 μm in one dimension and 5–100 μm in the other two dimensions.

2. A composition according to claim 1, wherein the boron ester is boron triethoxide or tripropoxide.

3. A composition according to claim 1, further comprising an alkoxide and/or fluoride of a GpIA or GpIIA metal.

4. A composition according to claim 1, wherein the GpIVB metal is titanium.

5. A composition according to claim 1, wherein the one or more metals of the metal alkoxide is Ti, Zr or Al or (i) Zr, Ti; (ii) Al, Ti, Na; (iii) Ti, Na, Zr; (iv) A, Ti, Zr; or (v) Al, Ti, ZR, Na.

6. A composition according to claim 1, wherein the filler comprises up to 30% by weight of the composition before curing.

7. A composition according to claim 1, wherein the filler is in the form of flat plates.

8. A composition according to claim 7, wherein the filler comprises talc or mica.

9. A composition according to claim 1, wherein the filler comprises laponite, zeolite, kaolinite or vermiculite.

10. A composition according to claim 1, wherein the filler is coated.

11. A composition according to claim 10, wherein the filler is coated with titanium dioxide, chromium oxide, ferric oxide or a mixture thereof.

12. A composition according to claim 1, having a molar proportion of water:boron of(¾ to 3):1.

13. A composition according to claim 1, wherein the solvent comprises a ketone or alcohol.

14. A composition according to claim 1, wherein, boron is at least 40 molar % based on the total of B+GpIA+Al+GpIVB+GpVB.

15. A composition according to claim 14, wherein GpIA is under 50 molar %.

16. A composition according to claim 14, wherein Al is from 5 to 15 molar %.

17. A composition according to claim 14, wherein Al+GpVB+GpIVB together is from 3–15 molar %.

18. A composition according to claim 14, wherein the molar % of Al+GpVB+GpIVB together does not exceed one-fifth of the boron.

19. A composition according to claim 1, further comprising a non-metallic glass former other than B.

20. A composition according to claim 1, being produced by a process including an ageing step comprised of admitting moisture to the composition at a rate under 1% of the rate in free air.

21. A process for producing a glassy coating, comprising applying a composition according to claim 1, to an object to be coated, and curing the coating.

22. A process according to claim 21, wherein the coating is applied at a thickness up to 30 μm.

23. A process according to claim 21, wherein the coating is cured by an energy input of 1 to 2000 mJ/mm$^2$.

24. A process according to claim 23, wherein the energy input is 20 to 500 mJ/mm$^2$ or is 500 to 2000 mJ/mm$^2$.

25. A process according to claim 21, wherein the coating is cured by irradiating only a part thereof at any one instant, and moving said part about the coating.

26. The process according to claim 21, wherein the object is a tooth and the composition further includes a pigment.

27. The process of claim 21, wherein the object is a tooth, and further including applying a cosmetic stain to the tooth prior to applying the composition.

28. The process of claim 21, wherein the object is a tooth.

29. A method according to claim 23, wherein the energy input to the coating is such as to temporarily or permanently vitrify the enamel or dentine.

30. A method according to claim 28, wherein said filler is so formulated as to appear a tooth colour in the coating.

31. A process according to claim 21, wherein said object is a patient's tooth.

32. A process for producing a glassy coating on a surface, comprising applying a sol gel composition to a thickness of 1–20 μm to the surface and curing the applied composition, characterised in that the sol gel composition comprises:

a hydrolyzable boron ester, a solvent, alkoxide(s) of: any one or more of Al, Gp VB metal and GP IVB metals, and a filler of flat particles which have a mean thickness of up to 3 μm and a mean size of 5–100 μm in the other two dimensions.

* * * * *